United States Patent
Saydam et al.

(10) Patent No.: US 10,266,404 B2
(45) Date of Patent: Apr. 23, 2019

(54) METHOD FOR OBTAINING COMBUSTIBLE GASES FROM ROCKS FOR ENERGY PRODUCTION

(71) Applicant: CHITLIG ENERJI URETIM VE PAZARLAMA A.S., Ankara (TR)

(72) Inventors: Ahmet Cemal Saydam, Ankara (TR); Amir Hadji Ali Ghandi, Ankara (TR)

(73) Assignee: CHITLIG ENERJI URETIM VE PAZARLAMA A.S., Ankara (TR)

( * ) Notice: Subject to any disclaimer, the term of this patent is extended or adjusted under 35 U.S.C. 154(b) by 0 days.

(21) Appl. No.: 15/853,882

(22) Filed: Dec. 25, 2017

(65) Prior Publication Data

US 2018/0354788 A1    Dec. 13, 2018

(30) Foreign Application Priority Data

Jun. 7, 2017  (TR) .................................. 201708407
Dec. 18, 2017  (TR) .................................. 201720651

(51) Int. Cl.

| | |
|---|---|
| *C01B 3/26* | (2006.01) |
| *C12P 5/02* | (2006.01) |
| *C09K 8/582* | (2006.01) |
| *C09K 8/68* | (2006.01) |
| *C10J 3/72* | (2006.01) |
| *C10L 3/06* | (2006.01) |
| *C10L 3/10* | (2006.01) |
| *C10G 1/04* | (2006.01) |

(52) U.S. Cl.
CPC ................ *C01B 3/26* (2013.01); *C09K 8/582* (2013.01); *C09K 8/68* (2013.01); *C10G 1/04* (2013.01); *C10J 3/723* (2013.01); *C10L 3/06* (2013.01); *C10L 3/10* (2013.01); *C12P 5/023* (2013.01); *C10L 2290/141* (2013.01); *C10L 2290/28* (2013.01); *C10L 2290/544* (2013.01)

(58) Field of Classification Search
CPC ... C01B 3/26; C09K 8/582; C09K 8/68; C10J 3/723; C12P 5/023
See application file for complete search history.

(56) References Cited

U.S. PATENT DOCUMENTS

| | | | | |
|---|---|---|---|---|
| 3,810,968 | A * | 5/1974 | Renault et al. ......... | C01C 1/028 423/356 |
| 4,036,943 | A * | 7/1977 | Huron .................... | B01D 53/50 423/243.06 |
| 4,548,700 | A * | 10/1985 | Bearden, Jr. ........... | C10G 1/086 208/108 |
| 4,740,215 | A * | 4/1988 | Dillon ................... | C10L 1/1905 44/398 |
| 7,198,107 | B2 | 4/2007 | Maguire | |
| 9,057,082 | B2 | 6/2015 | Debruyn et al. | |
| 2010/0076235 | A1* | 3/2010 | Reiling .................. | C01B 3/586 585/310 |
| 2013/0200008 | A1* | 8/2013 | Theivendran ............ | C02F 1/76 210/752 |

* cited by examiner

*Primary Examiner* — Imran Akram
(74) *Attorney, Agent, or Firm* — Gokalp Bayramoglu

(57) ABSTRACT

The present invention relates to a method for obtaining a plurality of combustible gases from a rock and producing energy using the combustible gases. The method allows the utilization of shale rocks which are practically just waste, and enables producing a plurality of hydrocarbons in an aerobic condition. Obtaining combustible gases using the method disclosed in the present invention reduces the usage of fossil fuels. Thus, it is more environment-friendly compared to using fuels.

5 Claims, 3 Drawing Sheets

METHOD FOR OBTAINING COMBUSTIBLE GASES FROM ROCKS FOR ENERGY PRODUCTION

CROSS REFERENCE TO RELATED APPLICATIONS

This application is based upon and claims priority to Turkey Patent Application No. TR201708407, filed on Jun. 7, 2017, and Turkey Patent Application No. TR201720651, filed on Dec. 18, 2017, the entire contents of which are incorporated herein by reference.

TECHNICAL FIELD

The present invention relates to a method of obtaining combustible gases especially from shale rocks, and producing energy using the gases.

BACKGROUND OF THE INVENTION

Electronic and mechanical apparatuses, which we use daily, require energy to operate. This required energy is presently acquired by using facilities such as nuclear energy plants, thermal energy plants, hydroelectric plants, natural gas cycle plants, wind turbines and solar fields. Even though some of these facilities are sources for renewable energy, majority of our daily energy need is met by using fossil fuels. As fossil fuels are not renewable resources, they will be exhausted in the near future. For this reason, there is a need for developing new, sustainable energy production methods.

Sedimentary rocks, which are one of the three main types of rocks, are the most abundant type of rock on the face of the earth. They cover approximately 75% of the face of the earth, and they cover approximately 8% of the crust of the earth. Igneous rocks (or metamorphic rocks) which are present on the face of the earth are fragmentized and disintegrated over time as they come across with climate events, and various external factors (such as river and flood waters, winds). The small pieces that are scattered this way are carried away, also by external factors, they build up on lake and sea areas which have a pit shape, and they are compressed there. The small parts which are deposited and compressed this way, form sedimentary rocks. Main sedimentary rocks are sand stones, clay stones, lime stones (and other carbonated rocks), evaporites (rock salts, halides, borates etc.), and coal, shale and chert from sedimentary rocks.

Getting renewable energy from waste materials due to ever-increasing energy needs and the danger of depletion of fossil fuels is an ongoing activity all over the world.

However, all the research is based on producing methane gas by bacteria in an anaerobic environment.

On the other hand, shale rocks might contain natural gas that is trapped inside. This gas is called shale gas. This shale gas that is trapped inside the shale rocks are different from the combustible gases obtained by the present invention in the sense of both their formations and their compositions. Additionally, drilling is required in order to extract the shale gases that are trapped inside the shale rocks. In the inventive application, though, the combustible gases can be obtained at any preferred location.

It is already known that methane and other hydrocarbons can be produced by bacteria. However, the bacteria need to ferment their food sources in an anaerobic environment in order to produce hydrocarbons. This fermentation process takes too long, and no oxygen should be present in the environment during the fermentation process. For this reason, flammable gases created by bacteria can not respond to intensive needs. For this reason, there is a need for a method which allows the rapid production of flammable gases in an oxygenated environment.

The United States patent document numbered U.S. Pat. No. 7,198,107 in the background of the invention relates to obtaining shale gases. In the said document, water is injected inside the shale rocks, and in this way, the gases that have been trapped inside the gas can be gathered.

The United States patent document numbered U.S. Pat. No. 9,057,082 in the background of the invention relates to obtaining hydrogen from materials that are carrying hydrocarbons. In the said document, it is aimed to increase the speed of the microbiologic activity by adding ammonium phosphate and yeast extract to the rocks which are rich in hydrocarbons. In the said document, the obtaining of hydrogen is realized in an anaerobic environment.

None of the documents in the state of the art disclose a method for obtaining combustible gases and producing energy as in the present application.

SUMMARY OF THE INVENTION

The object of the invention is to provide a method which allows the utilization of shale rocks, which are practically accepted as waste.

Another object of the invention is to provide a method which allows combustible gases to be obtained in an aerobic environment.

Yet another object of the invention is to provide a method for producing energy which reduces the use of fossil fuels, and thus, which is more environmentally friendly with respect to these fuels.

BRIEF DESCRIPTION OF THE DRAWINGS

The following figures provided for the method of obtaining combustible gases from rocks, and producing energy in order to fulfill the objects of the present invention.

DETAILED DESCRIPTION OF THE INVENTION

The inventive method of obtaining combustible gases from rocks, for the production of energy essentially comprises the very basic steps of;
  milling the components,
  reacting the milled components with oxalic acid,
  obtaining hydrocarbons such as methane, ethane, propane, butane, pentane, hexane, and their iso forms (isomers), as a result of this reaction, in an aerobic environment.

In the inventive method, those shale rocks that emerge as a waste and have to be removed in any open or closed coal mining due to their very low calorific value for energy production hence increase the cost of coal mining, are especially preferred. In the present invention, the components that can be used include, but are not limited to any of shale rocks, sub-bituminous coal, half-bituminous coal, bituminous shale, kerogenous shale, bituminous schist rocks, marl, tar sand, oil sand, chitin, lignin, Sahara dust, desert dust, and combination thereof. In the remaining parts of the specifications, compounds comprising one, multiple or all of the above-mentioned components will simply be named components. The milled components are then reacted with oxalic acid. As the result of this reaction, hydrocarbons such as methane, ethane, propane, butane, pentane, hexane, and their iso forms, are produced in an aerobic environment. Hydrocarbons are thus obtained in the oxygenated environment.

The station data, carried out under the framework of atmospheric greenhouse gas monitoring programs and open to the public, show that atmospheric carbon dioxide ($CO_2$) and methane ($CH_4$) have changed at the same time in the Sahara dust transport processes.

Figure 1:
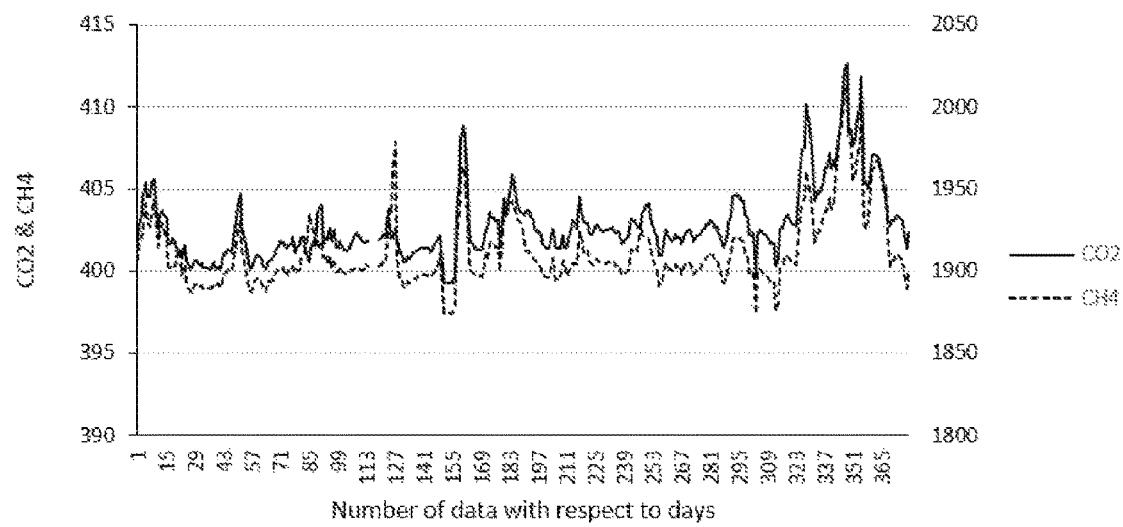
FIG. 1. The graph which shows the variations in CO2 and CH4, at Mace Head atmospheric monitoring station (West Ireland), as of February 2014.

For example, the change in $CO_2$ and $CH_4$, at Mace Head (MHD) atmospheric monitoring station which is located in the west of Ireland, as of February 2014, are shown (FIG. 1). As can be seen from this graph, both greenhouse gases are changing in perfect harmony. In other words, the changes in the atmosphere of both greenhouse gases are very similar. Where one is formed, the other is also formed in the same place and time.

The work we have done explains why and how the changes that occur in the process of Saharan dust transfer in the atmosphere create the $CO_2$ in the cloud.

These changes have been studied via the monitoring station that has been established at Ankara.

As we know the reason of the cause of the formation of $CO_2$ in the atmosphere, we have developed a hypothesis suggesting that the $CH_4$ which shows a simultaneous and totally parallel changes as $CO_2$, are being formed at the same source. However, the known or accepted fact in the scientific world is that methane can only be formed purely and simply in an anaerobic environment. However, as shown in FIG. 1, formation of $CO_2$ and parallel to that, the formation of $CH_4$ inside the cloud contradicts the current accepted science of $CO_2$ and $CH_4$ formation.

Our studies regarding the inventive application have picked up steam upon the assumption that the phenomenon which caused the said parallel change is the dusts that raised from the Sahara Desert. The basis of our studies starts with the interaction of oxalate with clay mineral, which is formed by the interaction of desert dust with cloud water during the dust transfer process. As a result of this reaction, Iron Oxalate is formed, and through a decarboxylation reaction, assisted by solar energy, $CO_2$ is formed. This formation has been numerously measured during the process of dust transport. It has been shown by that this formation is triggered by the oxalate, which is produced by the bacteria and fungi, upon their contact with the water inside the cloud droplet, during the long-distance transfer process of the dusts stemming from the desert. As a proof to this, it is shown that the said oxalate, and thus the decarboxylation products cannot be obtained using the specimens that are sterilized using $Co^{60}$ gamma radiation.

Figure 2:
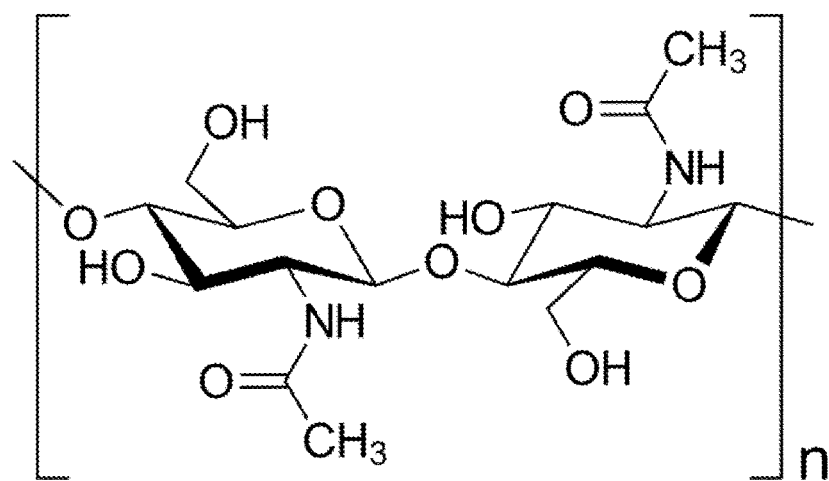
FIG. 2. Molecular structure of chitin.

The formation of methane, which shows parallel change to the carbon dioxide, in aerobic conditions directed us to investigating, in detail, the materials that are present in the soil. In our examinations, we have seen that the outer walls of the fungi are made of chitin. When the molecular structure of chitin (FIG. 2) is closely examined, it has been seen that the oxalate, which is naturally formed by the bacteria and fungi upon contact of the desert dusts with the water in the atmosphere, can also break down the chitin; and it is assumed that the methyl group, which is present in the molecular structure, can be converted to methane, and this assumption has been empirically investigated.

The experiments have been carried out with desert dust and water mixture. In order to eliminate the atmospheric contribution, the experiments have been carried out in controlled conditions which are named "headspace". The gas obtained as a result of the experiments was tested with pure methane gas at 1 and 15 ppmv.

Figure 3:
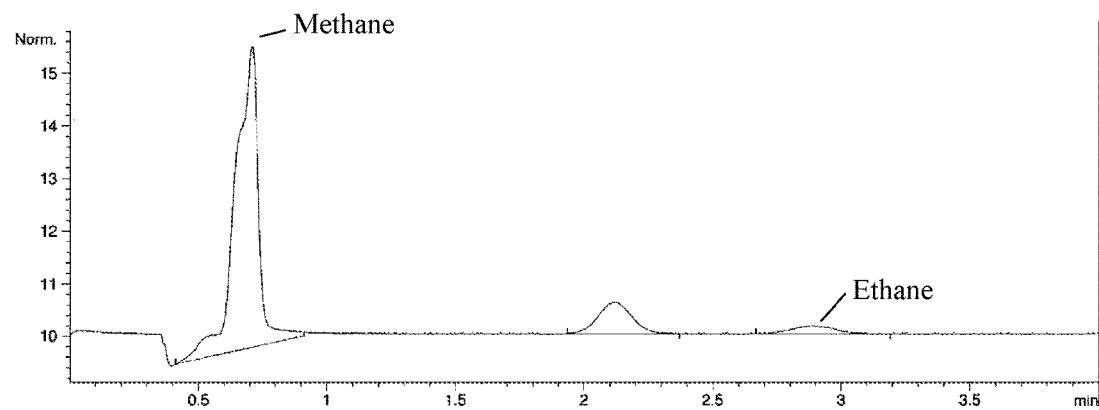
FIG. 3. A chromatogram showing methane formation in the headspace cups containing chitin and oxalic acid.

As can be seen from the chromatogram in FIG. 3, it has been empirically observed that the mixture of dust from Sahara Desert and water forms methane gas in a short time. In the process following, it has become definite that the Sahara dust produces methane, it has been hypothesized that the same phenomenon can be realized using natural chitin and lignin.

These experiments are later repeated using shale rocks and oxalate in "headspace" cups thus eliminating atmospheric interferences and the formation of methane, ethane, propane, buthane, pentane, hexane, and their isomers has been detected. Producing hydrocarbons such as methane, ethane, propane, buthane, pentane, hexane, and their isomers by reacting the shale rocks with the oxalic acid, has been neither known, nor used until now. This method provides an unexpected effect as it is unexpected for the hydrocarbons to form in an aerobic environment.

Figure 4:
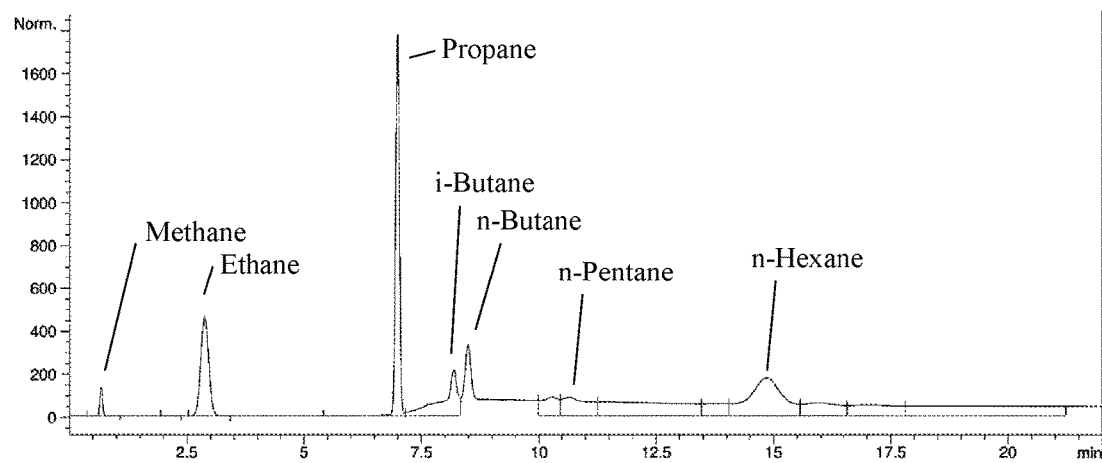
FIG. 4. A chromatogram showing that methane, ethane, propane, butane, pentane, hexane, and their isomers could be obtained from shale rocks with the help of oxalic acid.
Figure 5:
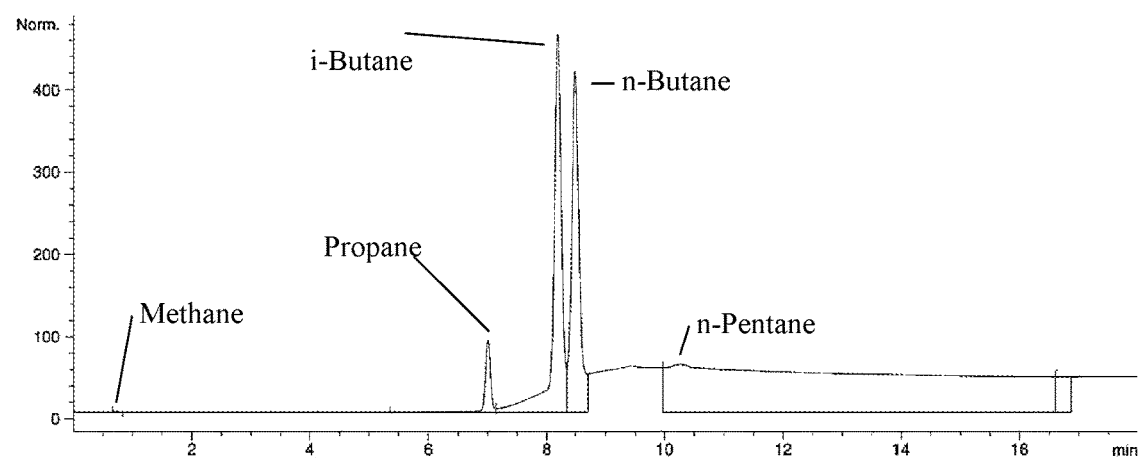
FIG. 5. A chromatogram belonging to a household propane cylinder.

In order to identify the obtained gases, they have been simply compared with the composition of the household tube gases. The chromatogram of household tube gas (FIG. 5), which is a mixture of propane and buthane overlaps perfectly with the chromatogram of the gases that have been produced from shale rocks (FIG. 4). This, in turn, proves the presence of propane and butane in the obtained gases.

In the performed experiments, it has also been investigated at which pH value should the used oxalic acid be. Even though it has been observed that the reaction takes place at every concentration of oxalic acid having a pH value below 7, it has been understood that the most suitable pH value is below 2.

It has also been observed in the conducted experiments that the mixture of ground shale rocks and oxalic acid can be realized at any ratio, and at any temperature.

Also, experiments using sub-bituminous coal, half-bituminous coal, bituminous shale, kerogenous shale, bituminous schist rocks, marl, tar sand, oil sand, chitin, lignin, Sahara dust, desert dust materials have been conducted experiments formation of hydrocarbons is observed when any of these materials are used.

The flammable gases obtained by the method of the invention can then be burned to produce heat and thus these gases can be used to generate energy.

These gases can be used especially in power plants using heat for producing electricity, such as natural gas cycle plants, coal power plants etc. By this way, the fossil fuels, which are used in the plants, can be substituted with a renewable source, and thus a more environmentally friendly energy production method is achieved.

The produced gases can also be used as fuel in internal combustion engines.

These gases can be used in all internal combustion or external combustion heat cycles.

The combustible gases obtained by the inventive method can be used in heat cycles by taking them directly into a combustion chamber or can also be stored for later usage.

It is also possible for the gases having longer chains, which are obtained by the inventive method, to be converted to other petrochemical raw materials using chemical techniques.

What is claimed is:

1. A method for obtaining combustible gases, wherein the method enables producing the combustible gases including a plurality of hydrocarbons in an aerobic environment, comprising:

milling a component to obtain a milled component, wherein the component is selected from the group consisting of shale rock, chitin, Sahara dust and a combination thereof;

reacting the milled component with an oxalic acid; and obtaining the plurality of hydrocarbons including methane, ethane, propane, butane, pentane, hexane, and their iso forms thereof in the aerobic environment at the end of the reaction.

2. The method for obtaining combustible gases of claim 1, wherein a pH value of the oxalic acid is below 2.

3. A method for producing energy, comprising:

producing a plurality of hydrocarbons using a heat cycle by milling a component to obtain a milled component, wherein the component is selected from the group consisting of shale rock, chitin, Sahara dust and a combination thereof, reacting the milled component with an oxalic acid, obtaining the plurality of hydrocarbons including methane, ethane, propane, butane, pentane, hexane, and their iso forms thereof in an aerobic environment at the end of the reaction; and producing energy from said hydrocarbons.

4. The method for producing energy of claim 3, wherein the heat cycle is an external combustion heat cycle.

5. The method for producing energy of claim 3, wherein the heat cycle is an internal combustion heat cycle.

* * * * *